US006309629B1

(12) United States Patent
Travkina et al.

(10) Patent No.: US 6,309,629 B1
(45) Date of Patent: Oct. 30, 2001

(54) WEAR RESISTANT COSMETIC COMPOSITIONS

(75) Inventors: Irina Travkina, River Edge; Maha Raouf, Franklin Lakes; Harold E. Pahlck, Waldwick, all of NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 09/461,447

(22) Filed: Dec. 14, 1999

(51) Int. Cl.[7] ............................ A61K 31/74; A61K 6/00; A61K 7/00; A61K 31/01; A01N 27/00

(52) U.S. Cl. ......................... 424/78.03; 424/401; 424/64; 514/762; 514/944

(58) Field of Search ............................... 424/64, 75, 76.8, 424/78.03, 401; 516/91, 47; 252/182.11; 514/944, 762

(56) References Cited

U.S. PATENT DOCUMENTS 4,699,780 10/1987 Jennings et al. ....................... 424/60
4,929,439 5/1990 Cotteret et al. .
4,935,228 * 6/1990 Finkenaur et al. ..................... 424/64
5,221,534 * 6/1993 DesLauriers et al. ............ 424/78.03
5,288,482 * 2/1994 Krzysik ................................. 424/64
5,318,775 * 6/1994 Shore et al. ........................... 424/64
5,352,441 * 10/1994 Mausner ................................ 424/64
5,707,612 1/1998 Zofchak et al. ........................ 424/69
5,849,275 12/1998 Calello et al. ......................... 424/64
6,103,221 * 8/2000 Arnaud et al. ......................... 424/59

* cited by examiner

*Primary Examiner*—Dameron L. Jones
*Assistant Examiner*—Lauren Q Wells
(74) *Attorney, Agent, or Firm*—Ohlandt, Greeley, Ruggiero & Perle, LLP

(57) ABSTRACT

There is provided a cosmetic composition, preferably in the form of a lip gloss composition, that is smooth, glossy, and wear resistant. The composition has an oil or liquid ester and a gel, and optionally, one or more waxes, one or more pigments, and one or more emollients.

17 Claims, No Drawings

WEAR RESISTANT COSMETIC COMPOSITIONS

BACKGROUND OF THE INVENTION

1. Field of the Invention

The present invention relates generally to cosmetic compositions. More particularly, the present invention relates to cosmetic compositions that are applied to the skin and lips, which offer enhanced ease of application and wear resistance, e.g. non-feathering and non-bleeding. In addition, the present invention provides cosmetic compositions that have features of traditional gloss products, namely high shine, even coverage, and light feel.

2. Description of the Prior Art

Traditional lipsticks are made of an oil or fatty base that is stiffened to a desired consistency with waxes of various types. The waxes serve to raise the melting point and improve the physical stability of the base. The color of the lipstick is ordinarily provided by insoluble pigments or lakes, which are finely dispersed in the base. In addition, a fluorescein dye derivative, such as tetrabromofluorescein, which stains the lips, may be incorporated into the base.

A lip gloss composition is a composition used for cosmetic and lip care purposes and specifically for lip coloring, in much the same manner as lipsticks are used. A lip gloss composition has a very high shine. Moreover, the lip gloss composition is commonly semi-solid, and has a fluid, smooth consistency. These characteristics are preferred by consumers in many situations.

However, lip gloss compositions are moved too readily on the surface of the lips. Such movement results in very low wear resistance. For example, lip glosses will accumulate in the fine creases in the skin of the lips and the skin immediately surrounding the lips. This tendency is called feathering, and is undesirable to consumers. Additionally, the oils contained in a lip gloss oftentimes cause the color to migrate beyond the outer perimeter of the lips, resulting in a halo effect. This tendency is called bleeding, and is undesirable to consumers.

Prior art examples of wear-resistant cosmetic compositions include U.S. Pat. No. 4,699,780 to Jennings, et al., titled Cosmetic Composition. The Jennings et al. patent provides for a composition comprising a resin, a polysiloxane, a polyolefin that is liquid at room temperature, and at least one hardening agent.

However, there is an ongoing need for cosmetic compositions, which may be used, for example, as lip gloss compositions, that combine high shine, fluidity, and smooth consistency with wear resistance and vibrant color.

SUMMARY OF THE INVENTION

It is an object of the present invention to provide a cosmetic composition, such as a lip gloss composition, that provides high gloss, fluidity, smooth consistency, long-lasting shine, and long-lasting color.

It is another object of the present invention to provide such a cosmetic composition that provides vibrant lip gloss colors combined with resistance to feathering and bleeding.

Accordingly, there is provided a cosmetic composition, preferably in the form of a lip gloss composition, that is semi-solid, glossy, long-lasting and wear resistant. The composition comprises a gel base, and optionally, one or more waxes, one or more colorants, and one or more emollients.

DETAILED DESCRIPTION OF THE INVENTION

The present invention provides a cosmetic composition, preferably a lip gloss composition, that is smooth, glossy, wear resistant and stable.

The cosmetic composition according to the present invention preferably comprises a gel base that is present in an amount about 75.0 percent to about 99.0 percent by weight (wt %) of the total weight of the composition. More preferably, the base is present in an amount about 80 wt % to about 90 wt % and, most preferably, about 80 wt %. Moreover, the cosmetic composition optionally comprises up to about 5.0 wt % of one or more waxes, up to about 15.0 wt % of one or more colorants, such as pigments, and up to about 20.0 wt % of one or more emollients.

The gel base includes a liquid ester or an oil, preferably non-polar, which can be either natural or synthetic, and a gellant. More preferably the oil or ester of the base is a non-polar, branched chain aliphatic hydrocarbon homopolymer and, most preferably, hydrogenated polyisobutene. Hydrogenated polyisobutene conforms generally to the formula:

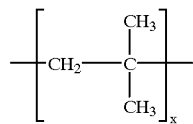

wherein x is an integer greater than 1.

The hydrogenated polyisobutene imparts emolliency, flexibility, and high gloss to the cosmetic composition.

The hydrogenated polyisobutene is preferably about 60 wt % to about 99 wt % of the gel base.

In addition, the gel base also includes one or more gellants in an amount about 1.0 wt % to about 40 wt % of the total weight of the gel base. More preferably, the total amount of gellant is present in an amount about 1 wt % to about 20 wt % of the total weight of the gel base and, most preferably, about 10 wt %.

The gellant(s) are preferably one or more block copolymers. These copolymers are set out in more detail in U.S. Pat. No. 5,221,534, which is incorporated herein by reference. A preferred hydrogenated mixed-block copolymer consists of (1) styrene (2-cyclohexa-3-diene); (2) ethylene; and (3) propylene or butylene monomers; or the derivatives thereof, having the general structures:

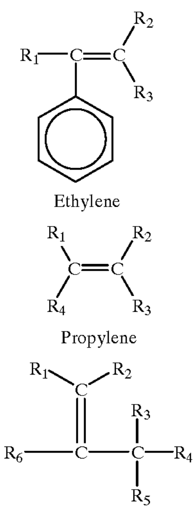

(iv)

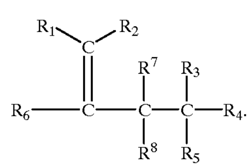

where $R_1$ to $R_8$ are each independently a hydrogen or a hydrophobic alkyl chain.

This hydrogenated mixed-block copolymer is known as, for example, a hydrogenated styrene/ethylene/propylene tri-block copolymer or a styrene/ethylene/butylene tri-block copolymer. The "blocks" of polymerized styrene monomers are mixed with "blocks" of polymerized ethylene and propylene or butylene monomers. Typically, this hydrogenated mixed-block copolymer acts as a film former, as well as a gellant, plasticizer, emollient and/or moisturizer. The gellants promote improved skin occlusivity and transepidermal water loss (TEWL). Clinical studies with gelled mineral oil have shown that moisturization as measured by TEWL improves 53% even though the gel base contains more than 90% mineral oil. It should be understood that one or more hydrogenated styrene/ethylene/propylene mixed-block block copolymers and/or styrene/ethylene/butylene mixed-block copolymers might be used in the present compositions.

A preferred hydrogenated block copolymer for use in the present invention is available from Penreco Technology Group, Karns City, Pa., and results in a clear gel base.

Since the cosmetic compositions, such as lip glosses, have a fluid and smooth consistency, the viscosity of the gel base should be about 50,000 centipoise (cps) to about 160,000 cps at 25° C. when tested with a Spindle T-C at 5 rotations or revolutions per minute (rpm) and the color, based on ASTM D1500, should preferably have a value less than 0.5.

The present invention also comprises an antioxidant in an amount up to about 0.5 wt % of the total weight of the composition. More preferably, the antioxidant is present in an amount up to about 0.4 wt % of the total weight of the composition.

The antioxidant is preferably selected from the group consisting of: ascorbyl palmitate, butylated hydroxytoluene (BHT), butylated hydroxyanisole (BHA), tocopheryl acetate, and ascorbic acid. More preferably, the antioxidant is BHT.

BHT is a substituted toluene that conforms to the formula:

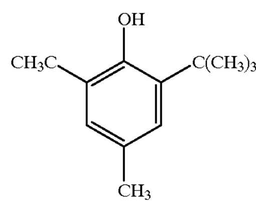

A cosmetic composition according to the present invention may be made without any wax. However, if waxes are included in the present composition, the amount of wax should be minimized to maintain the clarity of the composition. By maintaining a clear and transparent composition, ingredients for providing visual effects (e.g., glitter) may be incorporated into the composition. Similarly, a clear and colored composition will provide truer color to the composition. Accordingly, it is preferred that the amount of wax is only up to about 5 wt % of the total weight of the composition. More preferably, one or more waxes will be present in an amount about 1 wt % to about 3 wt % of the total weight of the composition to maintain such clarity. However, more wax can be used if clarity is not a concern.

The one or more waxes can be natural or synthetic waxes. Preferably, one or more microcrystalline waxes are used in the present invention. These microcrystalline waxes preferably have $C_8$ to $C_{50}$ hydrocarbons and a melting point preferably greater than about 60° C. (about 51° F.). Other waxes that can be used in the present invention are candelilla, carnauba, ozokerite, paraffin, polyethylene, beeswax, ceresin, hydrogenated castor oil, japan wax, or mixtures thereof.

Further, a cosmetic composition of the present invention may include colorants and emollients.

In a preferred embodiment, the cosmetic composition may include up to about 15.0 wt % of one or more colorants. More preferably, the colorants will be present in an amount about 8 wt % to about 12 wt % and, most preferably, about 10 wt % of the total weight of the cosmetic composition. Such colorants include pearls and pigments that are known in the art. For example, pigments used in the present invention may be metal oxide pigments, such as iron oxides and titanium oxides, FD&C dyes, D&C dyes, and lakes.

A cosmetic composition according to the present invention may also contain one or more emollients other than the ingredients in the gel base in an amount up to about 20.0 wt % of the total weight of the cosmetic composition. More preferably, emollients will be present in an amount about 2 wt % to about 15 wt % of the total weight of the cosmetic composition and, most preferably, about 5 wt %. Emollients useful in the present invention include any known to the art, including, but not limited to, oils and esters, such as lanolin and petrolatum.

In addition, a cosmetic composition according to the present invention may comprise other ingredients and additives known in the art, depending on the purpose for which the formulation is intended. For example, a lip gloss according to the present invention may optionally include one or more vitamins, sunscreens, fillers and fragrances.

The following is an example of a cosmetic composition according to the present invention.

EXAMPLE 1

Lip Gloss

| Ingredient | Wt % |
|---|---|
| Hydrogenated polyisobutene/ hydrogenated styrene-ethylene-propylene copolymer/BHT | 80 |
| Film Former | 4 |
| Wax | 3 |
| Colorants | 10 |
| Preservative | 0.1 |
| Fragrance | 0.3 |
| Emollients | q.s. |

This formula provides superior resistance to feathering and bleeding, as well as long-lasting shine and color, as a direct result of the thickening property achieved through the gel base. This thickening property also serves to drastically reduce the settling rate of the dispersed pigment particles by physically restraining the movement of the particles. In addition, the polymer system, itself, can confer an additional element of stabilization to the composition further enhancing the overall stability of the composition.

The present invention having been described with particular reference to the preferred forms thereof, it will be obvious that various changes and modifications may be made herein without departing from the spirit and scope of the invention as defined in the appended claims.

We claim:

1. A cosmetic composition comprising:

a gel base having a hydrogenated polymer and a gellant, said hydrogenated polymer being about 60.0 wt % to about 99.0 wt % of the total weight of said gel base, said gel base having a viscosity of about 50,000 cps to about 160,000 cps at 25° C.

2. The cosmetic composition of claim 1, wherein said gel base is about 75.0 wt % to about 99.0 wt % of the total weight of the cosmetic composition.

3. The cosmetic composition of claim 1, wherein said gellant is present in an amount about 1.0 wt % to about 40.0 wt % of the total weight of said gel base.

4. The cosmetic composition of claim 1, wherein said hydrogenated polymer is hydrogenated polyisobutene.

5. The cosmetic composition of claim 1, wherein said gellant is an hydrogenated mixed-block copolymer comprising monomers having a general formula selected from the group consisting of:

(i)

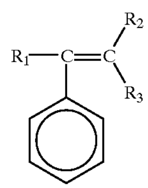

(ii)

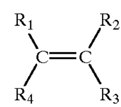

(iii)

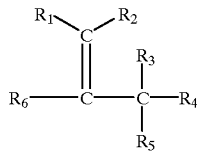

(iv)

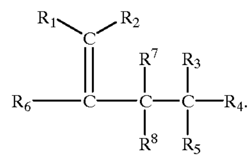

6. The cosmetic composition of claim 1, further comprising an antioxidant.

7. The cosmetic composition of claim 6, wherein said antioxidant is selected from the group consisting of: ascorbyl palmitate, BHT, BHA, tocopheryl acetate, ascorbic acid, and mixtures thereof.

8. The cosmetic composition of claim 6, wherein said antioxidant is present in an amount not more than about 0.5 wt % of the total weight of said composition.

9. The cosmetic composition of claim 1, further comprising one or more waxes.

10. The cosmetic composition of claim 9, wherein said one or more waxes are present in an amount up to about 5.0 wt %.

11. The cosmetic composition of claim 1, further comprising one or more colorants.

12. The cosmetic composition of claim 11, wherein said one or more colorants are present in an amount up to about 15.0 wt % of the total weight of the composition.

13. The cosmetic composition of claim 1, further comprising one or more emollients.

14. The cosmetic composition of claim 13, wherein said one or more emollients is present in an amount up to about 20.0 wt % of the total weight of the composition.

15. The cosmetic composition of claim 1, further comprising one or more ingredients selected from the group consisting of: vitamins, sunscreens, fragrances, fillers, and mixtures thereof.

16. A cosmetic composition having a gel base comprising:

a hydrogenated polymer;

a hydrogenated gellant; and butylated hydroxytoluene, wherein said gel base has a viscosity about 50,000 cps to about 160,000 cps at 25° C.

17. A method of providing improved feathering resistance and bleeding resistance to a lip gloss composition comprising adding to said composition a gel base having a hydrogenated polymer and a gellant, wherein said gel base has a viscosity of about 50,000 cps to about 160,000 cps at 25° C.

* * * * *